United States Patent [19]

Helland et al.

[11] Patent Number: 5,628,774
[45] Date of Patent: May 13, 1997

[54] CARDIAC LEAD WITH COMPOSITE INSULATING STRUCTURE

[75] Inventors: John R. Helland; Diane M. Muff, both of Redmond, Wash.

[73] Assignee: InControl, Inc., Redmond, Wash.

[21] Appl. No.: 429,886

[22] Filed: Apr. 27, 1995

[51] Int. Cl.$^6$ ........................................ A61N 1/05
[52] U.S. Cl. ........................................ 607/116; 607/122
[58] Field of Search .................. 607/116, 119, 607/122, 123, 132

[56] References Cited

U.S. PATENT DOCUMENTS 4,851,009  7/1989  Pinchuk ........................ 607/116
5,350,404  9/1994  Adams et al. ..................... 607/122

FOREIGN PATENT DOCUMENTS 4013358  6/1994  WIPO ........................... 607/119

*Primary Examiner*—William E. Kamm
*Attorney, Agent, or Firm*—Richard O. Gray, Jr.

[57] ABSTRACT

A lead for implantation in a human body exhibits improved combined biodegradation, blood surface compatibility, wear and flexibility characteristics. The lead includes at least one electrode and at least one connector connecting the electrode to a connector at the proximal end of the lead. An outer insulation surrounds the at least one conductor, and includes a first insulation formed of silicone encircling the at least one conductor, and a second insulation formed from polyurethane encircling the silicone rubber insulation.

7 Claims, 2 Drawing Sheets

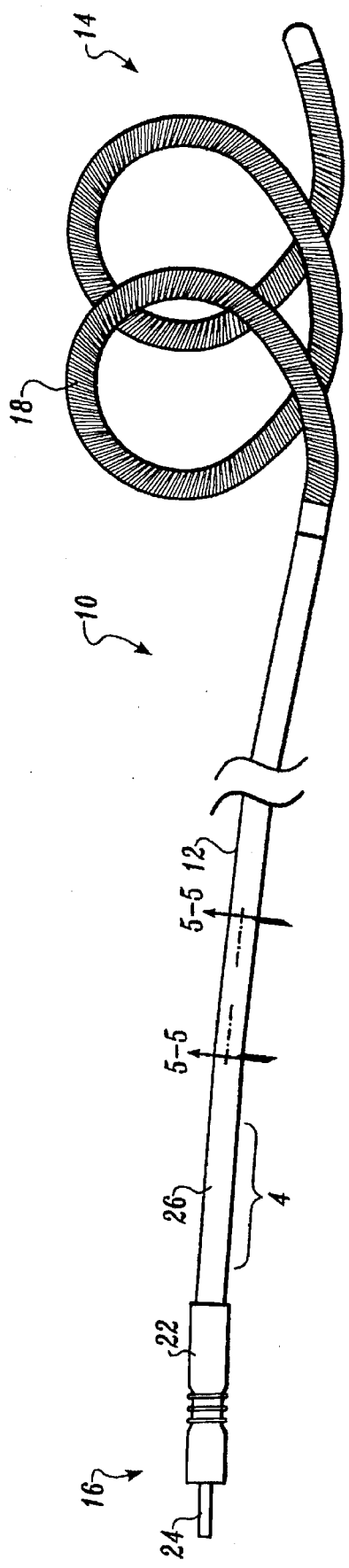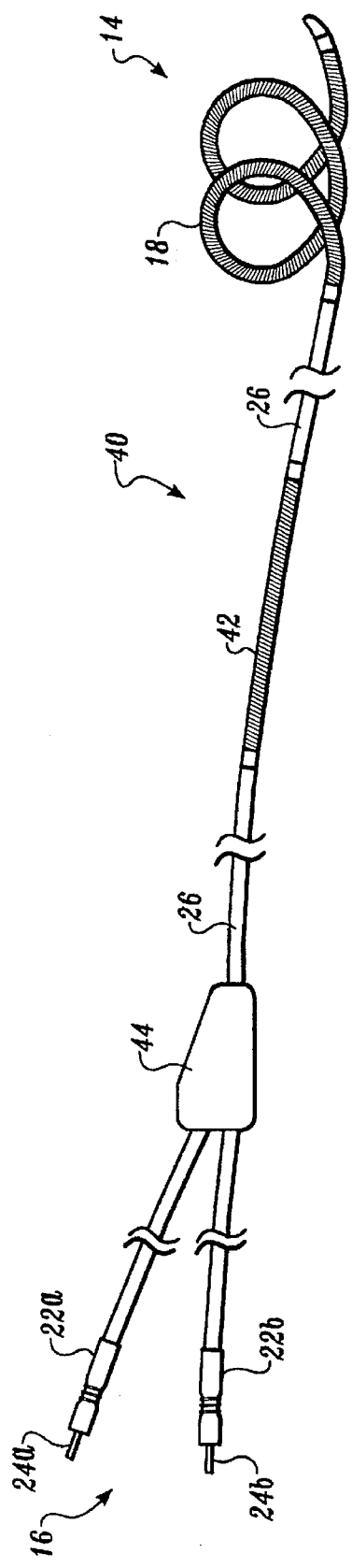

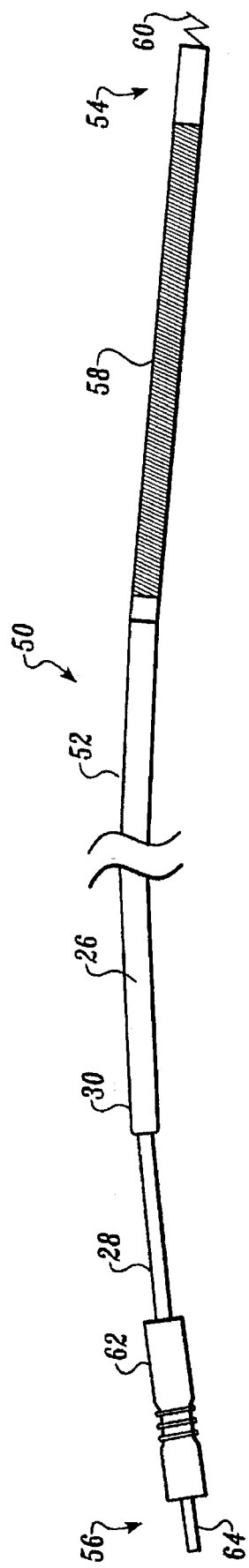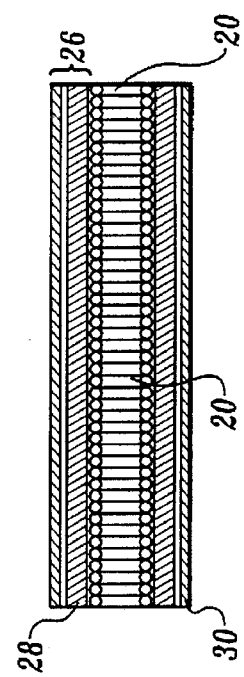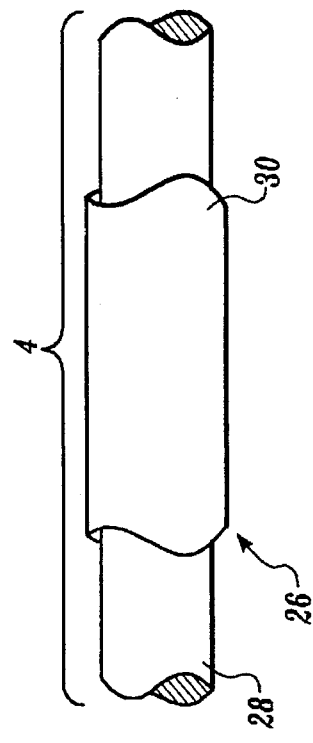

CARDIAC LEAD WITH COMPOSITE INSULATING STRUCTURE

BACKGROUND OF THE INVENTION

The present invention generally relates to a lead for implantation in a human body and for use with an implantable cardiac device, such as a pacemaker or cardiovertor/defibrillator. The present invention is more particularly directed to such a lead having a composite insulating structure formed from two different insulating materials, one overlying the other, which results in a lead having superior overall characteristics including, for example, improved mechanical properties, improved resistance to biodegradation, and improved blood surface compatibility.

Implantable leads for implantable cardiac devices, such as pacemakers and cardiovertors/defibrillators, are well known. Such a lead generally includes one or more electrodes for making electrical contact with a patient's heart, a connector for connecting the lead to the implantable device, and one or more conductors for coupling the electrode or electrodes to the connector. The lead also includes an outer insulation for electrically insulating the conductor or conductors so that only the electrodes may make electrical contact with the patient's body tissue. Ideally, the outer insulation for this intended use should possess a number preferred characteristics.

One such characteristic relates to flexibility. Generally, the more flexible a lead is, the less trauma is induced to the patient's tissues by implanted lead pressure. The flexibility of lead insulation is an important factor in the overall flexibility of a lead. Hence, it is highly desirable for the lead insulation to be flexible.

Another preferred characteristic of such insulators relates to their mechanical properties. It is preferable that such insulators have good tensile properties so that, in spite of unavoidable manipulation of a lead during implant, the structural integrity of the lead is maintained. It is further preferable that the outer insulation material have resistance to abrasive wear in the event that the lead rubs against another lead, another implanted device, or anatomical structure while in use after implantation.

Biostability is another characteristic important to implantable leads, and more particularly to the insulation material used as the lead outer insulation. Biostability relates to the ability of a lead insulation material to resist degradation in the implant (in vivo) environment. Of the many in vivo degradation mechanisms believed to exist, two such mechanisms, known to be mechanisms common to certain insulation materials, such as polyurethane, and considered to be most prominent, are environmental stress cracking (ESC) and metal ion induced oxidation (MIO). ESC is characterized by surface cracks in the insulation, believed to be produced by a combined interaction of the environment (internal body fluids) acting on the insulation, and stress on the insulation material. MIO is an accelerated degradation from reaction with metal ions, such as cobalt ions, chromium ions or the like, used alone or in alloy form in lead conductors.

Still another preferred characteristic of an insulation for implantable lead use is blood surface compatibility. This relates to the degree in which the surface provided by the insulation material contributes to the formation of blood clots around the lead. An insulation which presents a highly blood compatible surface is one which contributes little to blood clot formation. Generally, an insulator which provides a highly blood compatible surface is desirable for implantable lead applications.

Another surface phenomenon associated with implantable leads, and more particularly with the outer insulations used in such leads, is the coefficient of friction of the insulation in blood. Leads which incorporate insulators having a low coefficient of friction in blood are easier to implant because such leads more readily slide against each other and into veins and arteries. As a result, a low coefficient of friction in blood is a preferred characteristic for insulators used in forming implantable cardiac leads.

The two most common polymeric materials used for outer insulation in implantable leads today are silicone and polyurethane. Each type of material exhibits its own unique set of positive and negative properties for use in implantable cardiac leads.

Silicone exhibits superior flexibility. It also is highly biostable, being essentially impervious to ESC and MIO.

Silicone, however, does exhibit some disadvantages. For example, silicone has rather inferior mechanical properties. More particularly, it has rather poor tensile and wear characteristics. In addition, silicone does not provide a surface which is as compatible in blood as some other materials. It also has a rather high coefficient of friction in blood.

Polyurethane, for use as an insulation in implantable cardiac leads, has its own set of advantages. It has good mechanical properties in terms of tensile, toughness and wear characteristics. The mechanical properties of polyurethane are so good that leads using polyurethane as an outer insulation can be made to have thin insulator wall constructions, permitting small lead outer diameter dimensions to be obtained. It also provides a highly blood-compatible surface which can minimize clotting. It also has a very low coefficient of friction in blood, rendering polyurethane outer insulation leads much easier to slide into an artery or vein during implantation than, for example, outer insulation silicone leads.

Polyurethane, however, is not without its disadvantages for implantable lead use. It generally is not as biostable as other materials, such as silicone. Some forms of polyurethane are reportedly especially susceptible to MIO and ESC. Polyurethane, in general, and some forms of polyurethane specifically, are considered to be stiffer than desirable for implantation use.

From the foregoing, it can be seen that the prior art implantable leads, using either silicone alone or polyurethane materials alone for outer insulation, have both positive characteristics and unavoidable negative characteristics. Leads incorporating silicone insulation are comparatively biostable because silicone is resistant to ESC and MIO. On the other hand, they have inferior mechanical properties (tensile, toughness and wear) and provide a surface having neither high blood surface compatibility nor a low coefficient of friction in blood. Leads incorporating polyurethane insulation have good mechanical properties (tensile, toughness, wear). Further, such leads provide a highly blood-compatible and low coefficient of friction surface. However, polyurethane is not highly biostable and is generally, comparatively stiff. A lead incorporating either material alone is therefore a compromise.

As will be seen hereinafter, the present invention provides a lead for implantation in the human body which overcomes the above-noted disadvantages in the prior art. More particularly, the lead of the present invention provides a composite insulating structure, formed of at least two different materials, resulting in lead performance which capitalizes on all of the advantages of the insulating materials utilized while, at the same time, negating the disadvantages of each of the insulating materials.

SUMMARY OF THE INVENTION

The invention therefore provides a lead for implantation in a human body. The lead includes a lead body and electrode means carried by the lead body for establishing electrical contact with the human body. The lead body includes a conductor contacting the electrode means, a first insulation surrounding and immediately adjacent to the conductor, and a second insulation surrounding and immediately adjacent to the first insulation. The first insulation and second insulation are formed of different insulating materials. The first insulation may be formed of silicone and the second insulation may be formed of polyurethane.

The present invention further provides a lead for implantation in a human body wherein the lead includes at least one electrode, at least one conductor contacting the at least one electrode, a silicone insulation encircling the at least one conductor, and a polyurethane insulation encircling the silicone insulation.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

FIG. 1 is a side plan view of a first implantable cardiac lead embodying the present invention, the lead including a single electrode at the distal end thereof;

FIG. 2 is a side plan view of a second implantable cardiac lead embodying the present invention, the second lead including a pair of electrodes;

FIG. 3 is a side plan view of a third implantable cardiac lead embodying the present invention, the third lead being particularly adapted for implantation in a chamber of the heart;

FIG. 4 is a partial side plan view, with a portion broken away, and to an enlarged scale to illustrate the composite outer insulating structure of the leads of FIGS. 1–3, in accordance with the present invention; and, FIG. 5 is a cross-sectional view, to an enlarged scale, taken along lines 5—5 of FIG. 1.

DETAILED DESCRIPTION OF THE PREFERRED EMBODIMENTS

Referring now to FIG. 1, it illustrates a first lead 10 embodying the present invention. The lead 10 and the second and third leads 40 and 50, illustrated in FIGS. 2 and 3 respectively, are all implantable cardiac leads and primarily adapted for use with an implantable atrial defibrillator/cardiovertor, as described, for example, in U.S. Pat. No. 5,350,404, issued on Sep. 27, 1994, for LEAD SYSTEM FOR USE WITH AN ATRIAL DEFIBRILLATOR AND METHOD, which is assigned to the assignee of the present invention and incorporated herein by reference. As those skilled in the art will appreciate, the present invention is equally as applicable to any type of implantable lead for use with any type of implantable cardiac device, such as pacemakers or ventricular defibrillators/cardiovertors, for example.

The lead 10 of FIG. 1 includes a lead body 12 having a distal end 14 and a proximal end 16. An elongated electrode 18 is carried on the lead body 12 at the distal end 14. A conductor 20 (FIG. 5), in the form of a stylet coil, is connected to the electrode 18 and couples the electrode 18 to a pin 24 of a connector 22, carried at the proximal end 16 of the lead 10. The connector 22, as will be appreciated by those skilled in the art, serves to couple the lead 10, and more specifically the electrode 18, to internal circuitry of an implantable cardiac device, such as an implantable atrial defibrillator/cardiovertor as contemplated herein.

The lead body 12, in addition to the conductor 20, includes an outer insulation 26. A section 4 of the lead body 12 is more particularly illustrated in FIG. 4. As will be noted in FIG. 4, the outer insulation 26 includes a first insulation 28 and a second insulation 30. By making further reference to FIG. 5, it can be seen that the first insulation 28 encircles or surrounds the conductor 20, and the second insulation 30 encircles or surrounds the first insulation 28. Also, the first insulation 28 is immediately adjacent to the conductor 20, and the second insulation 30 is immediately adjacent the first insulation 28. In accordance with the embodiment of FIG. 1, the first and second insulations are co-extensive, forming a composite outer insulation structure, extending from the electrode 18 to the connector 22.

Referring now to FIG. 2, it illustrates a second lead 40 embodying the present invention. The second lead 40 is similar to the lead 10 of FIG. 1, except that it includes a second electrode 42. Hence, like reference characters are used in FIG. 2 for like elements as shown in FIG. 1. The lead 40 includes a lead body 44 having a distal end 14 and a proximal end 16. An elongated electrode 18 is carried on the lead body 44 at the distal end 14. The conductor 20 (FIG. 5) connects the electrode 18 to a pin 24a of a connector 22a carried at the proximal end 16 of the lead 40. The second electrode 42 is carried by the lead body 44 intermediate the electrode 18 and the connector 22. As would be appreciated by those skilled in the art, a second conductor (not shown) may be coaxially disposed in relation to the conductor 20 for coupling the electrode 42 to a second pin 24b of a second connector 22b. The connectors 22a and 22b are provided separate from each other so that each may be independently coupled to its own corresponding connector socket of an implantable cardiac device, such as an implantable atrial defibrillator/cardiovertor as contemplated herein.

The outer insulation 26 extends from a bifurcation 44 to the second electrode 42, and from the second electrode 42 to the first electrode 18. Also, the outer insulation 26 preferably takes the form, as illustrated in FIGS. 4 and 5, to include the first insulation 28 and the second insulation 30. Hence, it is preferred that the first and second insulations 28 and 30 be co-extensive between the bifurcation 44 and the electrode 42, and between the electrode 42 and the electrode 18. However, in accordance with broader aspects of the present invention, the second insulation 30 may be segmented to cover selected portions of the lead 40 to serve as one or more protective sleeves. In doing so, the first insulation 28 would be relied upon for providing electrical insulation and biostability. The protective sleeves, on the other hand, may be relied upon for their mechanical properties, such as abrasive wear resistance.

The lead 10 of FIG. 1 and the lead 40 of FIG. 2, as described in the aforementioned U.S. Pat. No. 5,350,404, are particularly adapted for implantation in the coronary sinus and great cardiac vein of the heart to dispose the electrode 18 in the coronary sinus and great cardiac vein adjacent the left atrium. As also taught in the aforementioned referenced patent, a preferred path for implanting the leads 10 and 40 extends down the superior vena cava, into the right atrium, through the ostium of the coronary sinus, into the coronary sinus, and to the great cardiac vein to place the electrode 18 in the coronary sinus and great cardiac vein of the heart. With respect to lead 40, the electrodes 18 and 42 are preferably displaced on the lead body 44 such that when the electrode 18 is in the coronary sinus and great cardiac vein, the electrode 42 resides in the right atrium.

The lead 50, illustrated in FIG. 3 and to which reference is now directed, is particularly adapted for implantation in the right atrium of the heart for use in atrial cardioversion/ defibrillation in conjunction with the first lead 10 of FIG. 1. The lead 50 includes a lead body 52 having a distal end 54 and a proximal end 56. An elongated electrode 58 is carried on the lead body 52 at the distal end 54. A conductor, such as the conductor 20 (FIG. 5), couples the electrode 58 to a pin 64 of a connector 62 at the proximal end 56 of the lead body 52. The lead 50 may be implanted by being fed down the superior vena cava to the right atrium. This places the electrode 58 in the right atrium. To assist in anchoring the lead 50 in the right atrium, the distal end 54 includes a helical projection 60 for anchoring the distal end 54 of the lead in a manner known in the art.

The lead body 52 includes a composite outer insulation 26 extending proximally from the electrode 58, and preferably having the construction shown in FIGS. 4 and 5. To that end, the first insulation 28 extends from the electrode 58 to the connector 62 while the second insulation 30 extends proximally from the electrode 58 and terminates at a point intermediate the electrode 58 and the connector 62. Alternatively, the second insulation 30 may be configured to extend co-extensively with the first insulation 28 so as to also extend from the electrode 58 to the connector 62.

With respect to the composite insulation structure 26 of leads 10, 40 and 50, and in accordance with the present invention, the first insulation 28 and the second insulation 30 are formed of different insulating materials, not including different compositional variations of the same type material as described, for example, in U.S. Pat. No. 5,375,609. For example, the first insulation is preferably formed from silicone, such as Silicone Q7-4765, manufactured by Dow Corning Co. of Midland, Mich., or MED-4765, manufactured by NuSil Technology of Carpenteria, Calif., and the second insulation is preferably formed from polyurethane having a durometer of, for example, 55D, such as Pellethane 2363-55D, manufactured by Dow Chemical Co. of Midland, Mich. As used herein, the term "silicone" is meant to relate to any of the versions of silicone rubber polymers suitable for implantation. Also, as used herein, the term "polyurethane" is meant to relate to any of the versions or family types of polymers, known generically as polyurethanes, which are suitable for implantation.

The silicone first insulation preferably has an outer diameter of 0.061 inch and a wall thickness of 0.012 inch. The polyurethane second insulation preferably has an outer diameter of 0.079 inch, and a wall thickness of 0.006 inch. The polyurethane insulation tubing may be disposed over the silicone insulation tubing by first coating the outer surface of the silicone tubing with isopropyl alcohol to reduce the friction of the silicone to polyurethane, and then quickly sliding the polyurethane tubing over the silicone.

Silicone, as previously mentioned, is more biostable than polyurethane. As a result, the silicone first insulation 28 will provide both biostability and electrical insulation for the leads. Hence, the leads 10, 40 and 50 capitalize on the biostability characteristics of the silicone insulation. At the same time, the rather inferior biodegradation characteristics of the polyurethane insulation 30 are minimized or negated because the silicone insulation 28 protects the polyurethane insulation 30 from the biodegradation effects of failure mechanisms, such as MIO.

In addition, because the wall thickness of the silicone first insulation 28 is greater than the wall thickness of the polyurethane second insulation 30, and because the flexibility of a lead is largely dependent upon the flexibility of its outer insulation, the leads 10, 40 and 50 will have a flexibility which is only slightly less than the flexibility of silicone alone, and which is much greater than the flexibility of commonly used polyurethanes alone at comparable thicknesses. As a result, the leads 10, 40 and 50 capitalize on the flexibility of the silicone insulation which, at the same time, negates the inflexibility of the polyurethane insulation.

In addition, the polyurethane second insulation 30 will present a highly compatible surface to the blood. As a result, the leads 10, 40 and 50 will capitalize on the blood surface compatibility characteristics of the polyurethane insulation, while negating the rather poor blood surface compatibility characteristics of the silicone insulation.

Similarly, the polyurethane second insulation 30 capitalizes on its greatly lower coefficient of friction in blood and negates the much higher coefficient of friction in blood of silicone. In fact, it has been reported in the literature that the coefficient in blood of silicone is nearly twenty times the coefficient in blood of polyurethane. As a result, the present invention results in a lead which slides much more readily in an artery or vein, or against other leads, during implantation, as compared to a lead having silicone insulation alone.

In addition to all of the foregoing, the resulting leads 10, 40 and 50 also capitalize upon the durability of the polyurethane insulation in terms of tensile, toughness and wear characteristics. Because the polyurethane is the outermost insulation, these characteristics are capitalized upon while the rather poor characteristics of silicone, in terms of tensile, toughness and wear characteristics, are negated.

Lastly, because the silicone first insulation 28 provides resistance to biodegradation and electrical isolation, polyurethanes of softer durometer may be utilized to advantage as the second insulation 30 in accordance with the present invention. Polyurethanes having a durometer of, for example, 80A, which are softer than polyurethanes having a durometer of, for example, 55D, may be utilized in the second insulation 30. While polyurethanes of softer durometer generally are more susceptible to ESC and MIO, by being the most outer insulation layer, these insulations will be protected from MIO by the inner silicone insulation. Even if the outer insulation 30 should develop cracks due, for example, to ESC, the lead will still retain its superior mechanical characteristics while the first insulation 28 continues to provide biostability and electrical isolation. As a result, implantable lead constructions having improved combined characteristics, including flexibility, resistance to wear, ease of implant, blood surface compatibility and biodegradation, are rendered possible by the present invention.

While particular embodiments of the present invention have been shown and described, modifications may be made. For example, the present invention applies equally as well to implantable leads having one or more lumens for coupling lead electrodes to lead connectors. As a result, it is intended in the appended claims to cover all such changes and modifications which fall within the true spirit and scope of the invention.

What is claimed is:

1. A lead for implantation in a human body, said lead comprising:

at least one electrode;

a connector;

at least one conductor contacting the at least one electrode with the connector; and, an outer insulator including a silicone insulation encircling and immediately adjacent to the at least one conductor, and a polyurethane insulation encircling the silicone insulation and spaced from the at least one conductor by the silicone insulation.

2. A lead as defined in claim 1 wherein the at least one conductor has a length dimension between the connector and the at least one electrode and wherein the silicone insulation has a first length dimension coextensive with the at least one conductor length dimension.

3. A lead as defined in claim 1 wherein the silicone insulation has a first length dimension and wherein the polyurethane insulation has a second length coextensive with the first length dimension.

4. A lead as defined in claim 1 wherein the silicone insulation has a first length dimension and wherein the polyurethane insulation has a second length dimension which is smaller than the first length dimension.

5. A lead as defined in claim 4 wherein the at least one electrode includes a distal electrode and wherein the second length dimension extends proximally from the distal electrode.

6. A lead as defined in claim 1 wherein the lead includes a proximal end and a distal end, wherein the connector is positioned at the proximal end, wherein the at least one electrode includes a first electrode at the distal end and a second electrode intermediate the connector and the first electrode, and wherein the silicone insulation and the polyurethane insulation extend coextensively from the connector to the second electrode and from the second electrode to the first electrode.

7. A lead for implantation in a human body, the lead comprising:

a lead body;

a connector carried by the lead body; and electrode means carried by the lead body for establishing electrical contact with the human body, the lead body including a conductor contacting the electrode means with the connector, a first discrete insulation layer surrounding and immediately adjacent to the conductor, and a second discrete insulation layer surrounding and immediately adjacent to the first insulation, wherein the first insulation layer and second insulation layer are formed of different insulating materials and wherein the first insulation is formed of silicone and overlies all of the conductor, and wherein the second insulation is formed of polyurethane and includes at least one portion overlying less than all of the silicone first insulation.

* * * * *